(12) United States Patent
Govari

(10) Patent No.: US 10,145,760 B2
(45) Date of Patent: Dec. 4, 2018

(54) STATUS OF AN IRRIGATION PUMP

(71) Applicant: BIOSENSE WEBSTER (ISRAEL) LTD., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 303 days.

(21) Appl. No.: 14/988,176

(22) Filed: Jan. 5, 2016

(65) Prior Publication Data

US 2017/0191904 A1    Jul. 6, 2017

(51) Int. Cl.
| | |
|---|---|
| *G01F 17/00* | (2006.01) |
| *G01M 99/00* | (2011.01) |
| *A61M 3/02* | (2006.01) |
| *G01F 22/00* | (2006.01) |
| *A61M 5/152* | (2006.01) |

(52) U.S. Cl.
CPC ........ *G01M 99/008* (2013.01); *A61M 3/0237* (2013.01); *A61M 3/0254* (2013.01); *A61M 3/0258* (2013.01); *A61M 5/152* (2013.01); *G01F 22/00* (2013.01); *A61B 2218/002* (2013.01); *A61M 2205/3317* (2013.01); *A61M 2205/3379* (2013.01); *A61M 2205/50* (2013.01); *A61M 2205/52* (2013.01); *A61M 2205/70* (2013.01)

(58) Field of Classification Search
CPC ...... G01F 17/00; G01F 23/00; G01F 25/0061; G01M 99/008; A61B 18/12; A61B 18/18; A61B 2218/002; A61M 3/02; A61M 3/0237; A61M 3/0254; A61M 5/00; A61M 5/178; A61M 5/152; A61M 1/00; A61M 2205/3317; B01L 3/021
See application file for complete search history.

(56) References Cited

U.S. PATENT DOCUMENTS 5,342,313 A  *  8/1994  Campbell ................. A45F 3/20
                                                222/103
7,118,554 B2 * 10/2006  Sibbitt ................... A61M 5/284
                                                604/191
(Continued)

FOREIGN PATENT DOCUMENTS

| EP | 2322238 A1 | 5/2011 |
|---|---|---|
| EP | 3156084 A1 | 4/2017 |
| WO | WO 2014/030140 A1 | 2/2014 |

OTHER PUBLICATIONS

European Patent Office, Extended European Search Report, dated May 5, 2017, 9 pages.

*Primary Examiner* — Harshad R Patel
*Assistant Examiner* — Nigel Plumb

(57) ABSTRACT

A pump, including a compression compartment configured to receive, between first and second sides of the compartment, a flexible container holding a fluid and having an outlet; The pump also has a pump mechanism that is coupled to drive the first and second sides of the compartment together so as to force the fluid out of the container through the outlet. There are first and second electrodes the are fixed respectively to the first and second sides. The pump also includes a processor that is coupled to measure a capacitance between the first and second electrodes and to estimate, responsively to the capacitance, a volume of the fluid remaining in the container.

13 Claims, 6 Drawing Sheets

(56) References Cited

U.S. PATENT DOCUMENTS

| | | | | |
|---|---|---|---|---|
| 8,709,008 | B2* | 4/2014 | Willis | A61B 1/00089 |
| | | | | 606/41 |
| 9,833,284 | B2 | 12/2017 | Govari | |
| 2003/0136189 | A1* | 7/2003 | Lauman | A61M 1/1658 |
| | | | | 73/304 C |
| 2004/0082915 | A1* | 4/2004 | Kadan | A61B 1/00068 |
| | | | | 604/164.04 |
| 2006/0285986 | A1 | 12/2006 | Radgowski et al. | |
| 2010/0030209 | A1* | 2/2010 | Govari | A61B 18/1492 |
| | | | | 606/34 |
| 2011/0144639 | A1* | 6/2011 | Govari | A61B 18/1492 |
| | | | | 606/41 |
| 2013/0030426 | A1* | 1/2013 | Gallardo | A61B 18/1492 |
| | | | | 606/33 |
| 2014/0100518 | A1* | 4/2014 | Baxter | G01L 9/12 |
| | | | | 604/67 |
| 2014/0121657 | A1* | 5/2014 | Bar-Tal | A61B 18/18 |
| | | | | 606/33 |
| 2017/0325884 | A1* | 11/2017 | Govari | A61B 18/1492 |

\* cited by examiner

STATUS OF AN IRRIGATION PUMP

FIELD OF THE INVENTION

The present invention relates generally to pumps, and specifically to measuring the status of an irrigation pump that may be used in a medical procedure.

BACKGROUND OF THE INVENTION

Irrigation pumps are used in a wide range of fields, such as minimally invasive medical procedures. Examples of prior art techniques are provided below.

PCT Patent Publication WO 2014/030140, to Rogozinski, et al., whose disclosure is incorporated herein by reference, describes a fluid transference system, including: (a) at least two inflatable objects; (b) at least one variable-state fluid transfer conduit, interposed between a first and a second inflatable objects, the variable state conduit configured to allow fluid flow there-through in an open state and to disallow the flow in a closed state. Another fluid transfer system includes: (a) an entry port; (b) an exit port; (c) a unidirectional main conduit defined between the entry port and the exit port; (d) an intermediate port; and (e) an intermediate conduit defined between the intermediate port and the main conduit, intersecting the main conduit between a first unidirectional valve and a second unidirectional valve, the main conduit defining a unidirectional fluid flow.

U.S. Pat. No. 7,118,554, to Sibbitt, et al., whose disclosure is incorporated herein by reference, describes a syringe device comprising: a first syringe comprising: a first syringe barrel including a first opening at a distal end thereof through which fluid may be forced or aspirated; and a first syringe plunger sliding within the first syringe barrel for forcing fluid through the first syringe barrel opening, the first syringe plunger including a stopper at a distal end thereof which sealingly and slidably engages the first syringe barrel; a reciprocating member which moves along a track parallel to the axial direction of the first syringe; and a reciprocating device connecting the first syringe plunger to the reciprocating member so that when one member of the group consisting of the first syringe plunger and the reciprocating member moves distally, another member of the group is forced to move proximally.

U.S. Patent application publication 2004/0082915 A1, to Kadan, whose disclosure is incorporated herein by reference, describes a system for performing diagnostic needle arthroscopy and lavage through a single port of entry into the joint compartment. The system is comprised of a handpiece having valves for irrigation and suctioning, a diagnostic cannula attached to the handpiece. The system includes a mobile cart, camera, a high-resolution monitor and an air compressor to power individually controlled irrigation pumps to deliver irrigation fluid to a handpiece and a vacuum suction console to collect fluid.

U.S. Pat. No. 8,709,008, to Willis, et al., whose disclosure is incorporated herein by reference, describes visual electrode ablation systems which include a deployment catheter and an attached imaging hood deployable into an expanded configuration. In use, the imaging hood is placed against or adjacent to a region of tissue to be imaged in a body lumen that is normally filled with an opaque bodily fluid such as blood. A translucent or transparent fluid, such as saline, can be pumped into the imaging hood until the fluid displaces any blood, thereby leaving a clear region of tissue to be imaged via an imaging element in the deployment catheter. An electric current may be passed through the fluid such that it passes directly to the tissue region being imaged and the electrical energy is conducted through the fluid without the need for a separate ablation probe or instrument to ablate the tissue being viewed.

U.S. Patent application publication 20130030426 A1, to Gallardo, et al., whose disclosure is incorporated herein by reference, describes a catheter adapted for ablation which multiple dedicated irrigation tubings to supply fluid to their respective electrode or set of electrodes. The tubings provide parallel flow pathways through the catheter where irrigation fluid is delivered to irrigated tip and/or ring electrodes which can accomplish uni-polar or bi-polar ablation. Such separate and dedicated fluid pathways allow fluid to be delivered to the corresponding electrode or set of electrodes at different flow rates. An integrated ablation system using such catheter has an ablation energy source and an irrigation pump with multiple pump heads that can operate independently of each other. An integrated irrigation tubing set is included to extend between the fluid source and the catheter, with each pump head being able to act on a different tubing that delivers fluid to a different electrode or set of electrodes.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a pump, including:

a compression compartment configured to receive, between first and second sides of the compartment, a flexible container holding a fluid and having an outlet;

a pump mechanism coupled to drive the first and second sides of the compartment together so as to force the fluid out of the container through the outlet;

first and second electrodes fixed respectively to the first and second sides; and a processor coupled to measure a capacitance between the first and second electrodes and to estimate, responsively to the capacitance, a volume of the fluid remaining in the container.

Typically, the first and second electrodes form a non-parallel plate capacitor.

In a disclosed embodiment the processor is configured to measure an angle between the first and the second sides and to estimate, responsively to the angle, the volume of fluid remaining in the container.

In a further disclosed embodiment the first electrode includes a first single electrode covering at least 50% of the first side, and the second electrode includes a second single electrode covering at least 50% of the second side.

In a yet further disclosed embodiment the first electrode covers a first fraction of the first side, and is positioned at a first location in the first side, and the second electrode covers a second fraction of the second side, and is positioned at a second location in the second side, and the processor is configured to estimate the volume remaining responsively to the first fraction, the first location, the second fraction, and the second location.

In an alternative embodiment the first electrode covers a fraction of the first side, and is positioned at a location in the first side, and the second electrode includes a single electrode covering at least 50% of the second side, and the processor is configured to estimate the volume remaining responsively to the fraction and the location.

In a further alternative embodiment the pump includes a hinge, about which at least one of the first and second sides are configured to rotate.

In a yet further disclosed embodiment the fluid includes irrigation fluid used during an ablation procedure performed on a patient.

There is further provided, according to an embodiment of the present invention, a method, including:

configuring a compression compartment to receive, between first and second sides of the compartment, a flexible container holding a fluid and having an outlet;

coupling a pump mechanism to drive the first and second sides of the compartment together so as to force the fluid out of the container through the outlet;

fixing first and second electrodes respectively to the first and second sides; and measuring a capacitance between the first and second electrodes and estimating, responsively to the capacitance, a volume of the fluid remaining in the container.

The present disclosure will be more fully understood from the following detailed description of the embodiments thereof, taken together with the drawings, in which:

DETAILED DESCRIPTION OF EMBODIMENTS

Overview

The amount of fluid remaining in a fluid container supplying a pump may be measured by first measuring the volume of fluid in the container before the pump is activated, and tracking the volume of fluid used by the pump as it operates. While such a method is of course implementable, it may lead to erroneous results, for example if the original measurement is incorrect or if the tracked volume is incorrect.

Embodiments of the present invention measure the status of fluid remaining in a fluid container supplying fluid to a pump by a different method. The pump comprises a compression compartment formed of two sides, typically a first fixed side and a second side which rotates relative to the first side about a hinge. The compression compartment receives a flexible container holding the fluid and having an outlet. There is a pump mechanism which is coupled to drive the first and the second sides of the compartment together so as to force fluid out of the container through the outlet.

A first electrode is fixed to the first side, and a second electrode is fixed to the second side. A processor is coupled to measure a capacitance between the first and second electrodes, and the processor is configured to estimate, from the capacitance, a volume of fluid remaining in the container.

In some embodiments at least one of the first and second electrodes is formed as a rectangular array of electrodes. In this case the capacitance of a given electrode in the array may be used to estimate a volume of fluid remaining in the container that is in proximity to the given electrode.

Typically, embodiments of the present invention first undergo a calibration process, forming a correspondence between the measured capacitance of the first and second electrodes to the volume of fluid remaining in the container for different positions of the sides. The correspondence is used when the pump operates, to determine from the measured capacitance the volume of fluid remaining in the container.

System Description

Figure 1:
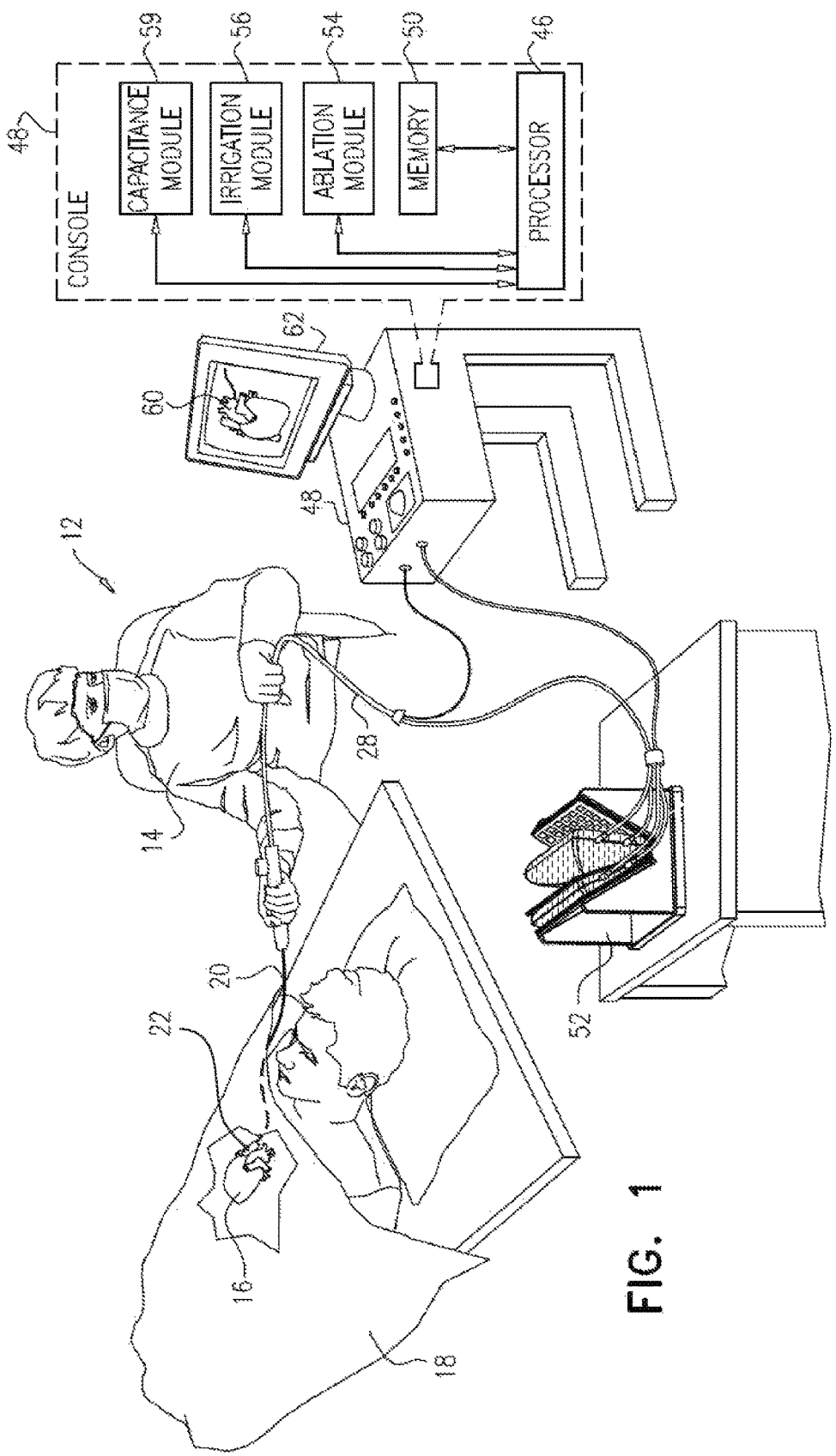
FIG. 1 is a schematic illustration of a pump status system, according to an embodiment of the present invention.

FIG. 1 is a schematic illustration of a pump status system 12, in accordance with an embodiment of the present invention. By way of example, the following description assumes that the system is used to determine the status of a medical pump supplying irrigation fluid to a catheter, but those having ordinary skill in the art will appreciate that the system may be used for determining the status of other pumps, such as those used for supplying chemical supplements in a drip irrigation system, and/or those supplying drugs.

System 12 may be used in a procedure that is performed by a medical professional 14, and, by way of example, system 12 is assumed to be used during an ablation procedure on a portion of a heart 16 of a human patient 18. In order to perform the ablation, medical professional 14 inserts a probe 20 into a lumen of the patient, so that a distal end 22 of the probe enters the heart of the patient. Distal end 22 comprises electrodes mounted on the outside of the distal end, the electrodes contacting respective regions of the heart. Probe 20 has a proximal end 28 connected to an operating console 48 and, in parallel, to an irrigation assembly 52 that provides irrigation fluid, typically saline solution, for the ablation procedure and that is described with reference to FIG. 2.

Irrigation assembly 52 delivers the fluid into an irrigation tube 86 (shown in FIG. 2), which transports the fluid to distal end 22 during the medical procedure. Assembly 52 is controlled by an irrigation module 56 that regulates the flow of the fluid to distal end 22 according to the irrigation requirements of the medical procedure. Module 56 may also use a capacitance module 59 that in turn is used to generate an indication of the status of the irrigation fluid provided by assembly 52. The functions of assembly 52 and modules 56 and 59 are described below.

System 12 is controlled by a system processor 46 located in operating console 48 of the system. During the procedure, processor 46 typically tracks a location and an orientation of distal end 22 of the probe, using methods known in the art. For example, processor 46 may use a magnetic tracking method, wherein magnetic transmitters external to patient 18 generate signals in coils positioned in the distal end. The Carto® system produced by Biosense Webster, of Diamond Bar, Calif., uses such a tracking method.

The software for processor 46 may be downloaded to the processor in electronic form, over a network, for example. Alternatively or additionally, the software may be provided on non-transitory tangible media, such as optical, magnetic, or electronic storage media. The track of distal end 22 is typically displayed on a three-dimensional representation 60 of the heart of patient 18 on a screen 62.

In order to operate system 12, processor 46 communicates with a memory 50, and with modules used by the processor to operate the system, including irrigation module 56, capacitance module 59, a tracking module (not shown in FIG. 1, but which operates the tracking method used by processor 46), and an ablation module 54. Ablation module 54 allows the processor to control parameters, such as the power used, of the ablation procedure. Irrigation module 56 enables processor 46 to control parameters such as a flow rate of the irrigation fluid during ablation. Capacitance module 59 enables the processor to determine the capacitance of a compartment of assembly 52. From the capacitance the processor determines the status of the irrigation fluid provided by assembly 52, the status comprising, inter alia, a volume of irrigation fluid remaining in a fluid container 72 or in a fluid container 74 (described in more detail below) used by assembly 52. For simplicity, other modules used by processor 46, which may comprise hardware as well as software elements, are not illustrated in FIG. 1.

Figure 2:
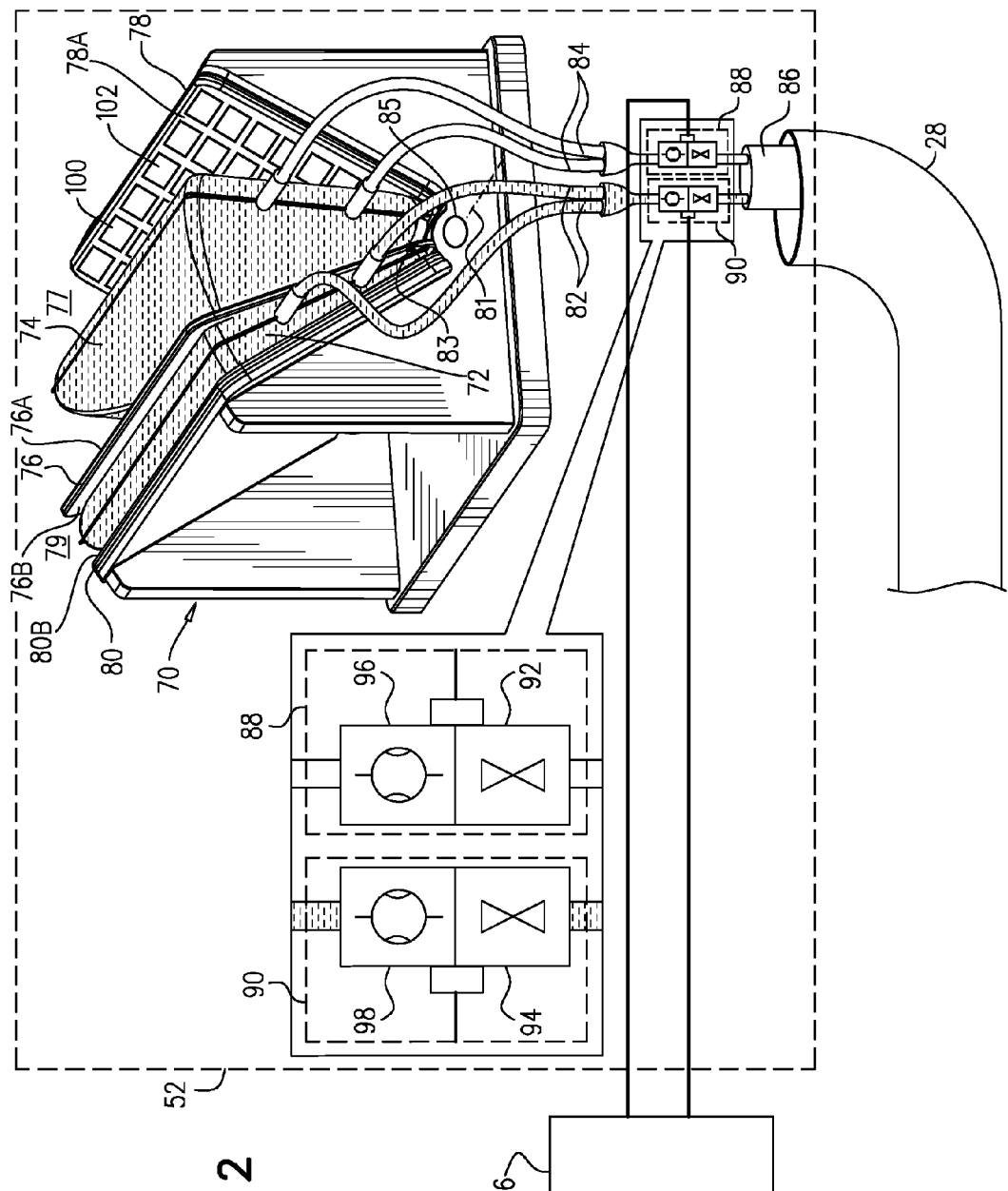
FIG. 2 is a schematic illustration of an irrigation system used in the system, according to an embodiment of the present invention.

FIG. 2 is a schematic illustration of irrigation assembly 52 in system 12, in accordance with an embodiment of the present invention.

The irrigation assembly comprises an irrigation pump mechanism 70. The pump mechanism is in the form of an open "hardcover book," and comprises two compartments formed by two walls (the two "covers" of the book) and a paddle 76 (corresponding to a page of the book) located between the walls. The paddle has two sides, a right side 76A and a left side 76B. A right compartment 77 is formed by a side 78A of a first wall 78, which is the "right cover" of the "hardcover book", and right side 76A of paddle 76. A left compartment 79 is formed by a side 80B of a second wall 80, which is the "left cover" of the "hardcover book", and left side 76B of paddle 76. The paddle pivots about a hinge 81 parallel to a junction between planes defining walls 78 and 80, (corresponding to the "spine" of the book) and oscillates between the walls by being driven by a motor 85. The motor of pump mechanism 70 is controlled by irrigation module 56. The use of the terms "right" and "left" in the above description of the pump is purely for clarity to differentiate the compartments, and it will be understood that the pump may operate in many different orientations.

Figure 3A:
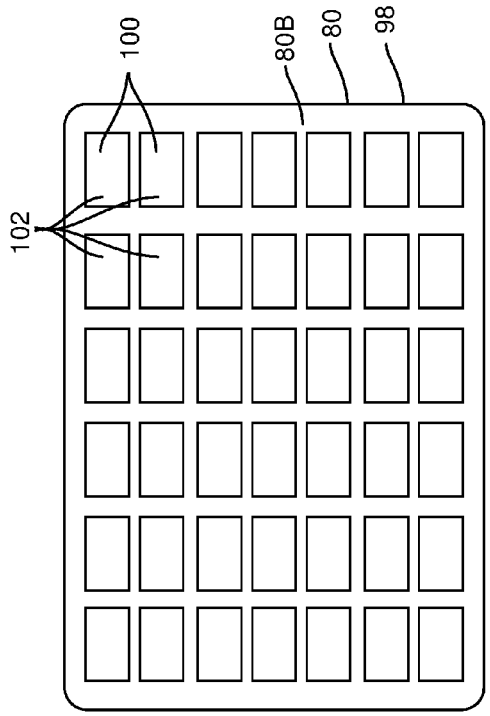
FIGS. 3A, 3B, 3C and 3D are schematic diagrams of sides of a wall and a paddle, according to an embodiment of the present invention.
Figure 3B:
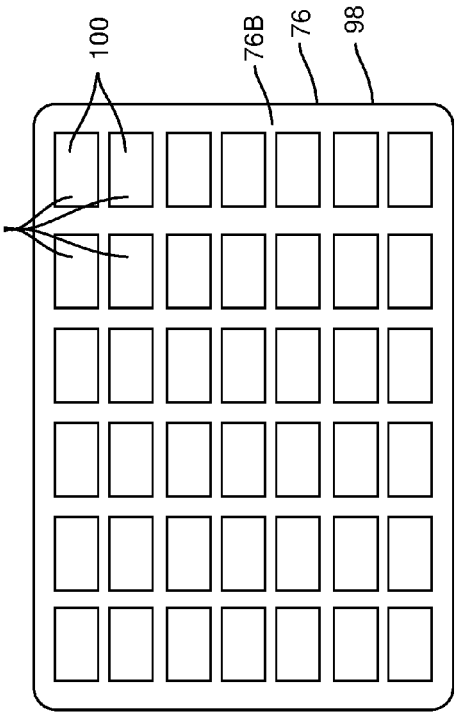
Figure 3C:
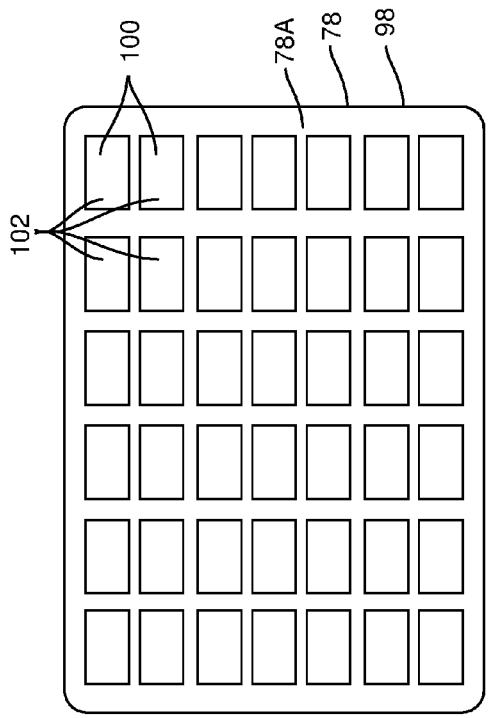
Figure 3D:
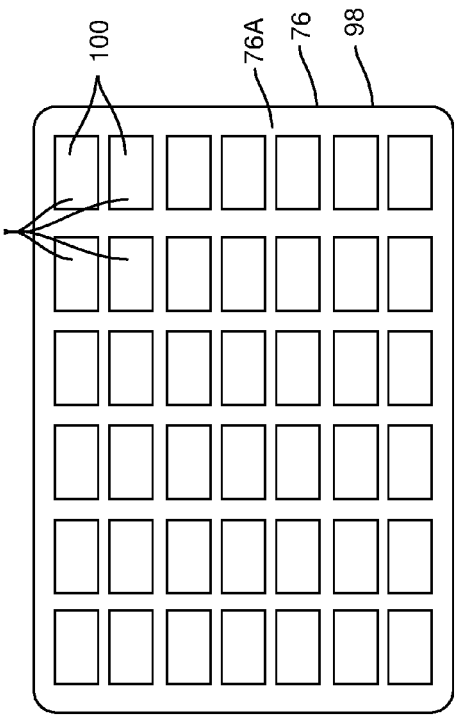
Figure 4A:
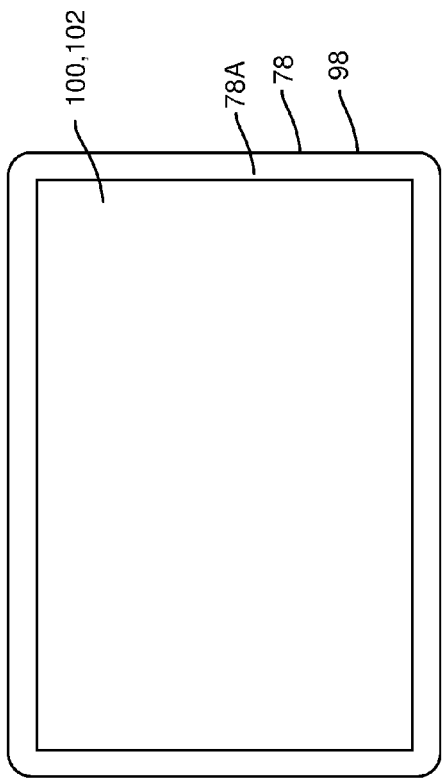
FIGS. 4A, 4B, 4C and 4D are schematic diagrams of sides of a wall and of paddle, according to an alternative embodiment of the present invention.
Figure 4B:
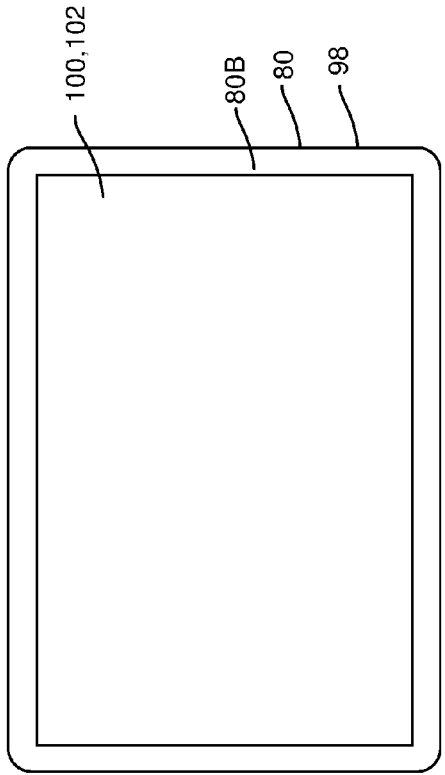
Figure 4C:
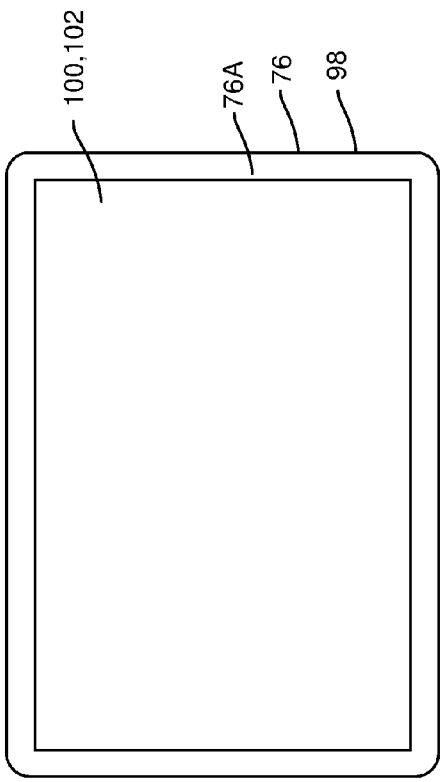
Figure 4D:
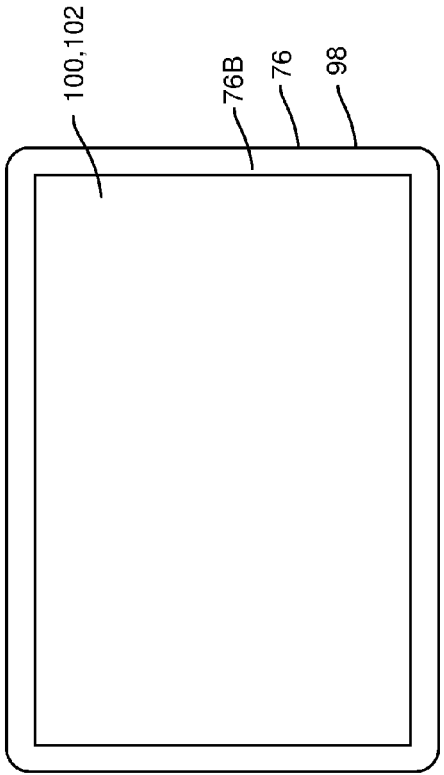

FIGS. 3A, 3B, 3C and 3D are respective schematic diagrams of side 78A of wall 78, side 80B of wall 80, right side 76A of paddle 76, and left side 76B of the paddle, according to embodiments of the present invention. (Elements of side 78A of wall 78 are also shown in FIG. 2.) Wall 78 (FIG. 3A) is typically formed of an inflexible insulating material 98, such as an acrylic, upon the side 78A of which is formed a rectangular array 100 of planar electrodes 102, insulated from each other. By way of example array 100 is shown in FIG. 3A as comprising seven rows, each row having six electrodes 102. However, it will be understood that array 100 may comprise any convenient number of rows greater than or equal to one, and any convenient number of columns greater than or equal to one. Each planar electrode 102 is typically connected by a respective lead (for clarity not shown) to capacitance module 59.

Wall 80 (FIG. 3B) is generally similar in structure to wall 78 (FIG. 3A), so that apart from the differences described below, elements indicated by the same reference numerals in both walls are generally similar in construction and in operation. In wall 80, an array 100 of planar electrodes 102 is formed on side 80B.

Paddle 76 and its sides 76A and 76B (FIGS. 3C and 3D) are also generally similar in structure to wall 78 and its sides (FIG. 3A), so that apart from the differences described below, elements indicated by the same reference numerals in the wall and its side and in the paddles and its sides are generally similar in construction and in operation. On side 76A, an array 100 of planar electrodes 102 is formed on the side; on side 76B, an array 100 of planar electrodes 102 is formed on the side.

It will be understood that, depending on the number of planar electrodes in array 100, the area of each electrode 102 is less than 50% of the area of the side wherein the electrode is formed. In the example of FIGS. 3A, 3B, 3C and 3D, the area of each electrode 102 is less than 2% of the side area.

FIGS. 4A, 4B, 4C and 4D are respective schematic diagrams of side 78A of wall 78, side 80B of wall 80, right side 76A of paddle 76, and left side 76B of the paddle, according to an alternative embodiment of the present invention. In the alternative embodiment illustrated in FIGS. 4A, 4B, 4C and 4D the two walls and the two sides of the paddle have only one electrode 102 in array 100, the single electrode substantially covering the walls and the paddle sides. Typically the coverage of the single electrode is at least 50% of the area of the walls and paddle sides.

The embodiments illustrated by FIGS. 3A, 3B, 3C and 3D, and by FIGS. 4A, 4B, 4C and 4D are two possible embodiments of the present invention, and others will be apparent to those having ordinary skill in the art. In the first embodiment, the four sides each have an array of seven rows of six electrodes. In the second embodiment, the four sides each have a single electrode. As is described in more detail with respect to the flowchart of FIG. 6 below, embodiments of the present invention measure for a given compartment of assembly 52 (FIG. 2) the capacitance between the one or more electrodes of the paddle side, and the one or more electrodes of the wall side, and from the capacitance estimate the volume of fluid remaining in the container retained in the compartment. Use of arrays of multiple electrodes also enables "granular" measurement of the volume of fluid, i.e., measurement of the volume in different portions of the container, whereas a single electrode in the paddle side and the wall side allows for no such granularity of measurement.

It will be appreciated that the granular measurements referred to above do not require that both arrays for a given compartment, on the paddle side and on the wall side, have multiple electrodes. Thus, it is sufficient for only one of the sides to have multiple electrodes, for example as a two-rows-by-two-columns array of electrodes, and the other side may have a single electrode.

Returning to FIG. 2, two fluid containers, also herein termed sacks, are placed in the right and left compartments to provide the irrigation fluid. A container 72 is placed in the left compartment, between wall 80 and paddle 76, and a container 74 is placed in the right compartment, between wall 78 and paddle 76. Each sack contains the irrigation fluid and two nipples that lead the fluid out of the sacks. A first pair of tubes 82 is connected to the nipples of sack 72 and a second pair of tubes 84 is connected to the nipples of sack 74.

In an embodiment, the two nipples of each sack are used for flow redundancy. In case one of the nipples is blocked, the other nipple of the sack directs the fluid into the respective tube. In another embodiment, each pair of tubes 82 and 84 merges into a single (wider) tube and connects to a flow control box. Tubes 82 are connected to a box 90, and tubes 84 are connected to a box 88.

Box 88 comprises a flow meter 96 and a valve 92. The flow meter measures the fluid flow in tubes 84, from sack 74 to irrigation tube 86. The valve controls the flow from sack 74 to irrigation tube 86, in an "open" state, and blocks the flow in a "close" state. Similarly, box 90 comprises a flow meter 98 and a valve 94. The flow meter measures the flow in tubes 84, from sack 72 to irrigation tube 86, and valve 94 controls the flow from sack 74 to irrigation tube 86, in an "open" state, and blocks the flow in a "close" state. In some embodiments each of the valves has the capability to regulate the flow in a tunable open state (e.g., wide open for fast flow and narrow open for slow flow). Boxes 88 and 90 are controlled by irrigation module 56, and the valves may be controllable automatically (by module 56), or manually (by a medical professional).

Before an ablation procedure, paddle 76 is rotated towards one of the walls, for example towards wall 78. As a result, the left compartment (between paddle 76 and wall 80) is able to receive a new sack filled with the irrigation fluid. Thus, sack 72 may be placed in the left compartment of pump 70. At this stage both valves 92 and 94 are closed and the irrigation assembly is ready for the ablation procedure.

When the ablation procedure starts, module 56 sends a first command to open valve 94, and a second command to activate the pump motor in order to rotate paddle 76 towards the left so as to compress sack 72 and transport the fluid from sack 72 to tubes 82. At this stage, the fluid flows in tubes 82 (while tubes 84 do not contain fluid). Flow meter 98 measures the flow and sends the readings to module 56, which regulates the compression force of paddle 76 on sack 72 by controlling the force of the pump motor. The required flow at meter 98 is dictated by the ablation module, and the irrigation module sets the flow (and thus the compression force on sack 72) accordingly.

Processor 46 uses a sensor 83 positioned at the hinge of pump 70 for measuring the angle of paddle 76 relative to walls 78 and 80. The readings of the sensor provide the processor with the angle between wall 78 and the paddle of left compartment 77, and with the angle between wall 80 and the paddle of right compartment 79. The angle for any given compartment is also referred to herein as the compartment angle, and is assumed to have a value θ.

As shown in FIG. 2, when most of the fluid outflows from sack 72, the right compartment is sufficiently open for placement of sack 74 (filled with irrigation fluid). As described herein, system 12 measures the volume of fluid remaining in a sack. When sack 72 is about to be empty, an alarm may be sent to module 56, which closes valve 94, opens valve 92, and reverses the direction of the motor in order to start compressing sack 74. At this stage the flow stops in tubes 82, and the fluid from sack flows in tubes 84. Module 56 receives flow readings from flow meter 96 and angle readings from the sensor in the hinge so as to control the flow rate of the ablation procedure, by controlling the angle of paddle 76, and by controlling the degree of open state in valve 92. (Professional 14 typically sets maximum and minimum threshold values for the flow rate.) Paddle 76 is rotated to the right (towards wall 78) and an operator (or a machine) may pull out empty sack 72, and replace it with a new sack once the left compartment is sufficiently open to contain a filled sack.

The oscillation of paddle 76 allows continuous flow of irrigation fluid into the distal end during the ablation procedure, without creating electrical noise in system 12. In addition, the pump structure provides a compact mechanism to deliver an unlimited volume of irrigation fluid with tight flow control according to the irrigation flow specification of the ablation procedure.

Figure 5A:
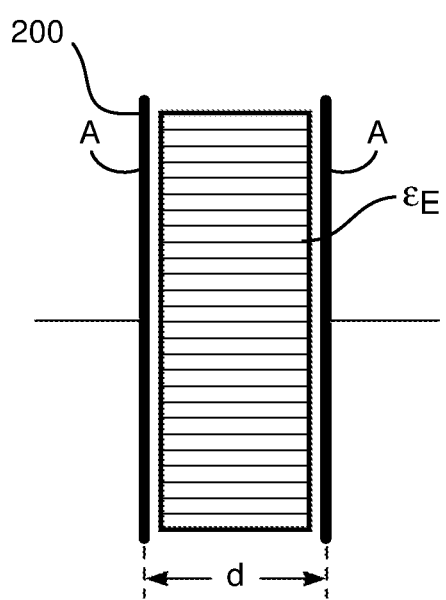
FIG. 5A is a schematic diagram of a parallel plate capacitor.
Figure 5B:
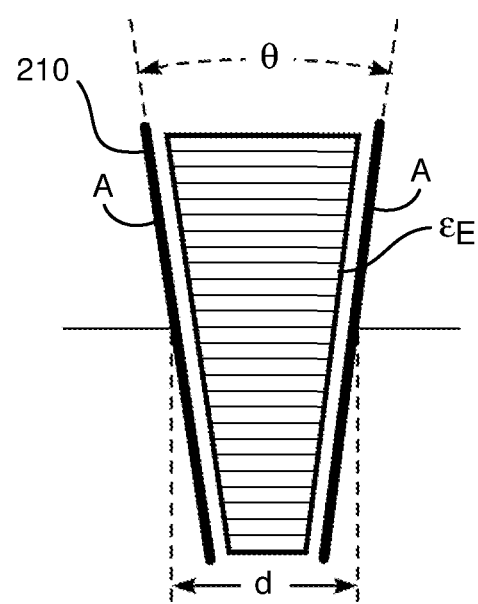
FIG. 5B is a schematic diagram of a non-parallel plate capacitor, according to embodiments of the present invention.

FIG. 5A is a schematic diagram of a parallel plate capacitor 200, and FIG. 5B is a schematic diagram of a non-parallel plate capacitor 210, according to embodiments of the present invention. While the capacitor formed by the electrodes of a given compartment is typically a non-parallel plate capacitor, because of the non-parallelism of the paddle and the wall, for simplicity the following discussion is directed to the properties of a parallel plate capacitor. It will be appreciated, however, that the conclusions of the discussion apply equally to parallel and non-parallel plate capacitors.

The capacitance of capacitor 200 is given by $$C = \frac{\varepsilon_0 \varepsilon_E A}{d} \tag{1}$$

where C is the capacitance in farads,
A is the area of the plates of the capacitor,
d is the distance between the plates,
$\varepsilon_0$ is the vacuum permittivity, and
$\varepsilon_E$ is an effective dielectric constant of the material between the plates.

The material between the plates of a compartment of pump mechanism 70 comprises air and saline solution. There are other materials, such as the container of the saline solution, but their contributions to the effective dielectric constant $\varepsilon_E$ are substantially constant and so are not considered further. Thus, an expression for $\varepsilon_E$ is given by:

$$\varepsilon_E = x \varepsilon_{saline\ solution} + (1-x) \varepsilon_{air} \tag{2}$$

where x is the fraction of the volume between the plates occupied by the saline solution,
$\varepsilon_{saline\ solution}$ is the dielectric constant of the saline solution, and
$\varepsilon_{air}$ is the dielectric constant of air.

Substituting equation (2) into equation (1) gives:

$$C = \frac{\varepsilon_0 (x \varepsilon_{saline\ solution} + (1-x) \varepsilon_{air}) A}{d} \tag{3}$$

For a given physical arrangement of capacitor 200, i.e., where values of A and d are known, and assuming that $\varepsilon_{saline\ solution}$ and $\varepsilon_{air}$ are also known, inspection of equation (3) shows that x can be determined if C is known. It will be appreciated that because $\varepsilon_{saline\ solution}$ is approximately 80, whereas $\varepsilon_{air}$ is approximately 1, values of C change significantly for relatively small changes of x, the fraction of the saline solution volume.

A similar equation to equation (3) applies for non-parallel capacitor 210. The physical arrangement of capacitor 210 is defined by the values of A, the area of the plates, d, the mean distance between the plates, and θ, the angle between the plates, corresponding to the compartment angle θ referred to above with reference to FIG. 2. For any given physical arrangement of capacitor 210, the same conclusion as for a parallel plate capacitor applies, i.e., assuming that ∈$_{saline\ solution}$ and ∈$_{air}$ are known, x can be determined if C, the capacitance of the capacitor 210 being considered, is known.

Figure 6:
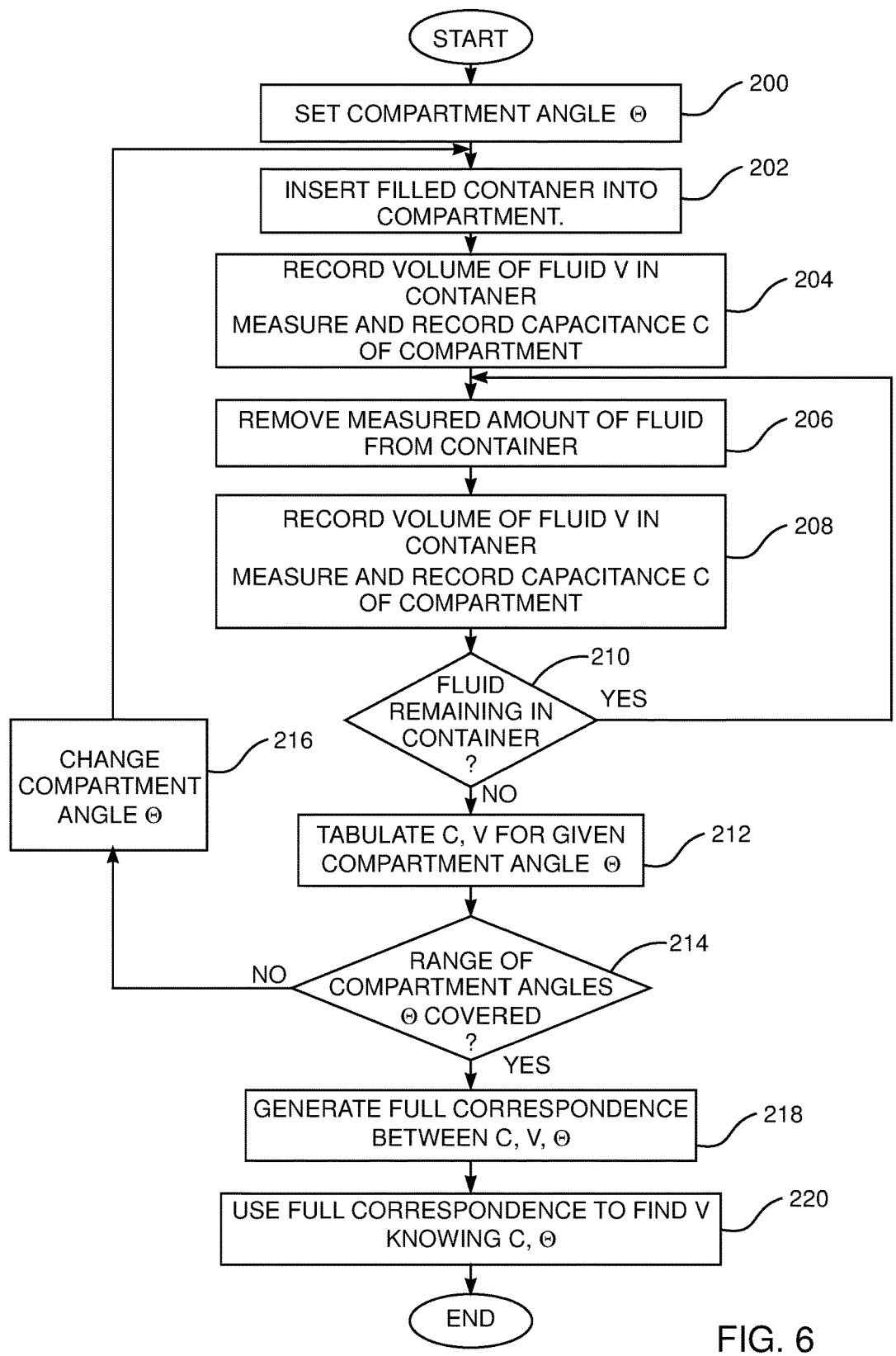
FIG. 6 is a flowchart of steps performed in operation of the pump status system, according to an embodiment of the present invention.

FIG. 6 is a flowchart of steps performed in operation of system 12, according to an embodiment of the present invention. The flowchart describes a procedure for determining the capacitance of a capacitor formed by a compartment of pump mechanism 70, and from the capacitance, the remaining volume of liquid in the compartment.

For simplicity, in the flowchart description each side of the compartment is assumed to have a single electrode, as described above with reference to FIGS. 4A, 4B, 4C and 4D, and the electrodes have an area A which substantially covers the sides. It will be understood that because the paddle and the wall of the compartment are coupled by hinge 81, compartment angle θ between the paddle and the wall is sufficient to also define a value of d, the mean distance between the two sides of the compartment. In an embodiment of the present invention, typical values of compartment angle θ are in a range of 10°-80°.

The flowchart is divided into two parts: a first part, comprising steps 200-218, describes a calibration process; a second part comprising step 220, describes how the calibration is used during operation of pump mechanism 70.

In an initial selection step 200, the compartment angle θ is set to a known value, herein by way of example assumed to be the largest value in the range of possible compartment angle values. Processor 46 records the value of the compartment angle.

In an insertion step 202, a completely filled fluid container is placed in the compartment. Typically, for large compartment angles, a container that has been completely filled in preparation for a procedure may be used. For smaller compartment angles, pump mechanism 70 may initially be operated on a completely filled container, to get to a completely filled container for the smaller compartment angle.

In a first measurement step 204 the processor records the value of the volume of fluid V in the container, and also operates module 59 to measure and record the capacitance C of the compartment.

In a volume change step 206 a measured amount of fluid is removed from the fluid container. The removal is controlled by valve 92 or 94, and may be manual or automatic, as described above with reference to FIG. 2.

In a second measurement step 208 the processor records the value of the volume of fluid V in the container, and measures and records the capacitance C of the compartment.

In a first decision step 210 the processor checks if there is fluid remaining in the container. If there is fluid remaining, the processor returns to step 206.

If there is no fluid remaining, in a continuation step 212 the processor prepares a correspondence between the values of C and V for the compartment angle, and proceeds to a second decision step 214.

In second decision 214 the processor checks if the range of possible compartment angles has been covered. If the range has not been covered, then in a change angle step 216 the processor changes the compartment angle θ, and returns to step 202.

If in decision 214 the range has been covered, then in a tabulation step 218 the processor prepares a correspondence between the values of C, V and all compartment angles θ. Typically the processor interpolates and extrapolates, using any convenient interpolation and extrapolation methods known in the art, between the values of C, V, and θ used in steps 204 and 208 so that the correspondence covers values of C, V, and θ not measured in the steps.

Tabulation step 218 is the final step in the calibration process begun in step 200.

In an operational step 220, processor 46 operates pump mechanism 70 as described above with reference to FIGS. 1 and 2. During the operation the processor measures the capacitance of the compartment of the mechanism being compressed, using capacitance module 59, and uses the correspondence generated in step 218 to determine the value of the volume V of fluid remaining in the compartment from the measured capacitance.

The processor may present the value of the remaining volume on screen 62 in a text and/or a graphic format, and/or use it for irrigation module 56 as described above, and/or use it for triggering events, such as a warning to professional 14.

For simplicity, the flowchart of FIG. 6 assumes that the electrodes of the sides of a compartment are single electrodes which substantially fill the sides. The resulting volume V determined in step 220 is thus the complete volume of fluid remaining in the compartment. In the case where at least one of the sides of the compartment has an array of electrodes, i.e., more than one row of electrodes or more than one column of electrodes, the capacitance between any given pair of electrodes of the two sides gives a measure of the fluid remaining in a region of the compartment determined by the locations of the two electrodes.

For example, if one of the sides of the compartment has a rectangular array of two by two electrodes, and the other side has a single electrode, then each electrode in the array may be used to give a measure of the fluid remaining in different portions of the compartment, as defined by the locations of the array electrodes, by measuring the respective capacitances between the array electrodes and the single electrode.

Assume that in this case the compartment is divided into top-left, top-right, bottom-left, and bottom-right portions. The steps of the flowchart of FIG. 6 may be adapted as follows.

During the calibration phase (steps 200-218), in steps 204 and 208 the processor adds the capacitances from each of the four electrodes of the array to give a single value of the capacitance. The single value is used in preparing the correspondence in step 218.

During the operational phase, step 220, the processor measures the capacitance between the single electrode and each of the four array electrodes. The processor uses the correspondence found in step 218, corrected by the fraction of the area of a given array electrode to the total area of the array electrodes, to find a volume of fluid remaining in the portion of the compartment in proximity to the given array electrode.

The processor may present the values of the remaining volumes on screen 62 in a variety of different formats, for example giving a total remaining volume, and/or giving a remaining volume for each of the portions of compartment. Typically in the latter case the presentation is graphic, for example as a two-by two array of rectangles having gray or color levels according to the value of the remaining volumes in the top-left, top-right, bottom-left, and bottom-right portions of the compartment.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A pump mechanism, comprising:
   two compartments formed by first and second walls with a paddle located between the first and second walls configured to receive in each of the two compartments,
   first and second flexible containers, each flexible container holding a fluid an having an outlet, the paddle having first and second paddle sides;
   a motor coupled to the paddle to drive the paddle towards one of the first and second walls together so as to force the fluid out of the container through the outlet;
   first and second electrodes fixed respectively to the first and second walls;
   third and fourth electrodes fixed respectively to the first and second paddle sides; and
   a processor coupled to the first, second, third and fourth electrodes to measure a capacitance between a pair of the first and third electrodes or second and fourth electrodes and to estimate, responsively to the capacitance, a volume of the fluid remaining in the respective flexible containers.

2. The pump mechanism according to claim 1, wherein the each pair of electrodes form a non-parallel plate capacitor.

3. The pump mechanism according to claim 1, wherein the processor is configured to measure an angle between the paddle with respect to one of the first and the second walls and to estimate, responsively to the angle, the volume of fluid remaining in one of the respective flexible containers.

4. The pump mechanism according to claim 1, wherein the first electrode comprises a first single electrode covering at least 50% of the first wall, and the second electrode comprises a second single electrode covering at least 50% of the second wall.

5. The pump mechanism according to claim 1, wherein the first electrode covers a first fraction of the first wall, and is positioned at a first location in the first wall, and wherein the second electrode covers a second fraction of the second wall, and is positioned at a second location in the second wall.

6. The pump mechanism according to claim 1, wherein the first electrode covers a fraction of the first wall, and is positioned at a location in the first wall, and wherein the second electrode comprises a single electrode covering at least 50% of the second wall.

7. The pump mechanism according to claim 1, wherein the paddle includes a hinge, about which the paddle is configured to rotate towards one of the first and second walls.

8. The pump mechanism according to claim 1, wherein the fluid comprises irrigation fluid used during an ablation procedure performed on a patient.

9. A method, comprising:
   configuring an assembly to receive, between first and second walls of the assembly, a paddle disposed between the first and second walls for placement of a first and second flexible containers, each container holding a fluid and having an outlet;
   coupling a motor to drive the paddle toward the first or second walls of the assembly together so as to force the fluid out of one of the containers through the respective outlets;
   fixing first and second electrodes respectively to the first and second walls and third and fourth electrodes on respective opposing sides of the paddle to define a first pair of electrodes with the first and third electrodes and a second pair of electrodes with the second and third electrodes; and
   measuring a capacitance between the first pair electrodes and second pair of electrodes and estimating, responsively to the capacitance of the respective pairs of electrodes, a volume of the fluid remaining in the respective flexible containers.

10. The method according to claim 9, wherein each of the first and second pairs of electrodes form a non-parallel plate capacitor.

11. The method according to claim 9, and comprising measuring an angle between the paddle with respect to one of first and the second walls and estimating, responsively to the angle, the volume of fluid remaining in the container disposed in the one of the compartments defined by the first wall, the paddle and the second wall.

12. The method according to claim 9, and comprising configuring the paddle to rotate about a hinge.

13. The method according to claim 9, wherein the fluid comprises irrigation fluid used during an ablation procedure performed on a patient.

* * * * *